(12) United States Patent
Qian et al.

(10) Patent No.: US 11,524,282 B2
(45) Date of Patent: Dec. 13, 2022

(54) REGENERATION METHOD FOR BENZENE ALKYLATION SOLID ACID CATALYST

(71) Applicant: Inner Mongolia Yitai Coal-based New Materials Research Institute Co., Ltd., Erdos (CN)

(72) Inventors: Zhen Qian, Erdos (CN); Jingwei Wu, Erdos (CN); Juncheng Li, Erdos (CN); Xiaolong Zhang, Erdos (CN); Hongcheng Cao, Erdos (CN); Yuan Gao, Erdos (CN); Xueting Wu, Erdos (CN)

(73) Assignee: Inner Mongolia Yitai Coal-based New Materials Research Institute Co., Ltd., Erdos (CN)

( * ) Notice: Subject to any disclaimer, the term of this patent is extended or adjusted under 35 U.S.C. 154(b) by 134 days.

(21) Appl. No.: 17/048,944

(22) PCT Filed: Jun. 11, 2019

(86) PCT No.: PCT/CN2019/090713
§ 371 (c)(1),
(2) Date: Oct. 19, 2020

(87) PCT Pub. No.: WO2020/103428
PCT Pub. Date: May 28, 2020

(65) Prior Publication Data
US 2021/0170378 A1    Jun. 10, 2021

(30) Foreign Application Priority Data
Nov. 21, 2018 (CN) .......................... 201811394576.5

(51) Int. Cl.
*B01J 29/90* (2006.01)
*B01J 38/56* (2006.01)
*C07C 2/66* (2006.01)

(52) U.S. Cl.
CPC ............... *B01J 29/90* (2013.01); *B01J 38/56* (2013.01); *C07C 2/66* (2013.01)

(58) Field of Classification Search
None
See application file for complete search history.

(56) References Cited

U.S. PATENT DOCUMENTS

| | | | | |
|---|---|---|---|---|
| 2004/0242404 A1* | 12/2004 | Hwang | ...................... | C07C 2/66 502/20 |
| 2011/0054232 A1* | 3/2011 | Sangar | ...................... | B01J 38/14 502/64 |

(Continued)

FOREIGN PATENT DOCUMENTS

| | | |
|---|---|---|
| CN | 1072353 A | 5/1993 |
| CN | 1281839 A | 1/2001 |

(Continued)

OTHER PUBLICATIONS

International Search Report issued in International Application No. PCT/CN2019/090713 dated Aug. 26, 2019 (2 pages).

(Continued)

*Primary Examiner* — Ali Z Fadhel
(74) *Attorney, Agent, or Firm* — Osha Bergman Watanabe & Burton LLP

(57) ABSTRACT

A regeneration method for a benzene alkylation solid acid catalyst, comprising: purging the solid acid catalyst in a reactor with a gas; continuously injecting n-hexane at a feed port of the reactor and heating the n-hexane to wash the solid acid catalyst, and discharging the n-hexane entraining benzene alkylation reaction residues from a discharge port of the reactor; and stopping injecting n-hexane, cleaning off a liquid in the reactor by purging with the gas, and cooling the reactor. In the regeneration method of the present disclosure, the regeneration liquid used is n-hexane, which can increase the solubility of the residues in channels and enhance the (Continued)

regeneration effect. Meanwhile, permanent damage to the channel structure of the catalyst caused by carbon burning regeneration can be avoided, thereby prolonging the lifetime of the catalyst.

11 Claims, 1 Drawing Sheet

(56) References Cited

U.S. PATENT DOCUMENTS

| | | | | |
|---|---|---|---|---|
| 2011/0077441 | A1* | 3/2011 | Iaccino | B01J 29/06 502/64 |
| 2012/0083637 | A1* | 4/2012 | Clem | B01J 38/02 502/34 |

FOREIGN PATENT DOCUMENTS

| | | | |
|---|---|---|---|
| CN | 1520928 | A | 8/2004 |
| CN | 1541768 | A | 11/2004 |
| CN | 1638870 | A | 7/2005 |
| CN | 1657161 | A | 8/2005 |
| EP | 1068898 | A2 * | 1/2001 ............. A61P 11/00 |
| EP | 1068898 | A2 | 1/2001 |
| WO | 2008038855 | A1 | 4/2008 |

OTHER PUBLICATIONS

Written Opinion issued in International Application No. PCT/CN2019/090713 dated Aug. 26, 2019 (4 pages).

Office Action issued in corresponding Chinese Application No. 201811394576.5 with English translation dated Oct. 10, 2020 (11 pages).

Wang, Zhi-Cai et al. "Synthesis of dodecylbenzene with benzene and 1-dodecene catalyzed by SO42-/ZrO2—TiO2" Journal of Molecular Catalysis (China) vol. 21, No. Feb. 1, 2007 (5 pages).

Jie, Ren et al. "Regeneration Method of Zeolite Catalyst for the Alkylation of Benzene with Long Chain Alkene" Journal of East China Institute of Chemical Technology, vol. 16, No. 6, Dec. 1990 (5 pages).

Second Office Action issued in corresponding Chinese Application No. 201811394576.5 dated Jan. 14, 2021 (12 pages).

Guo, Yanlin et al., "Organic Chemistry Experiments"; Tianjin University Press, p. 50; Aug. 31, 2018 (4 pages).

* cited by examiner

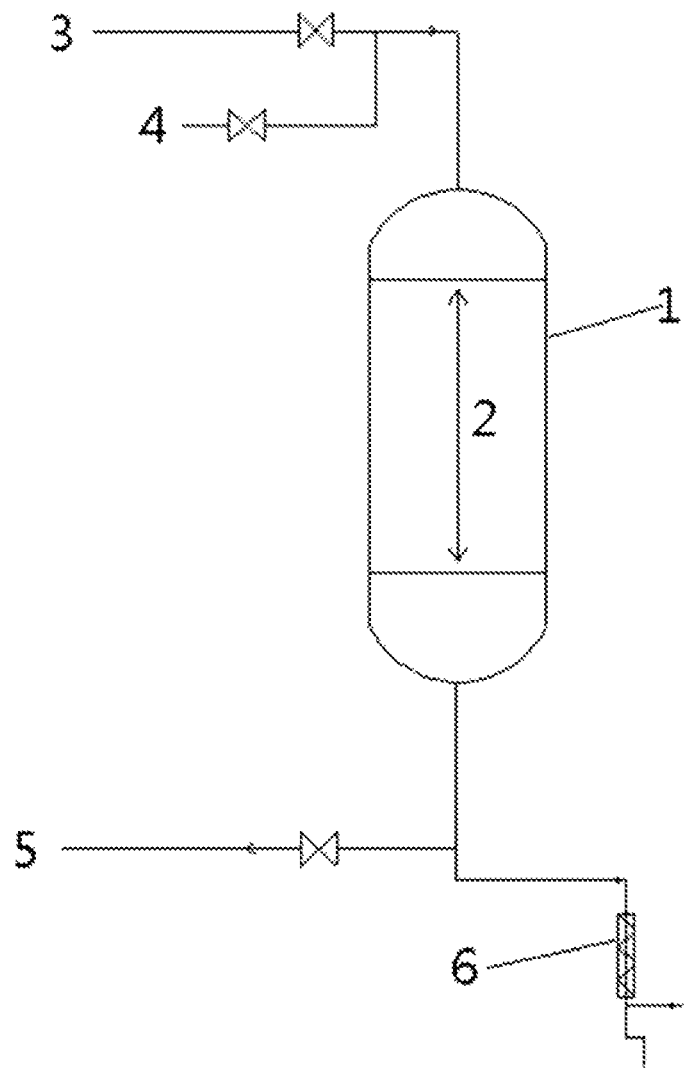

REGENERATION METHOD FOR BENZENE ALKYLATION SOLID ACID CATALYST

TECHNICAL FIELD

The present disclosure relates to the technical field of chemical engineering, and particularly to a regeneration method for a benzene alkylation solid acid catalyst.

BACKGROUND

Alkylbenzene is widely used in many fields. For example, linear alkylbenzene (LAB) is an important intermediate for producing a detergent. It is usually required to use solid acid catalyst in preparing alkylbenzene. Currently, industrialized solid acid process is the Detail process developed by UOP company. During the production of alkylbenzene, the raw materials as used are a mixture of an alkane and an alkene, and benzene. In the process, the isomerization and cracking products of the alkane and alkene will accumulate on the surface of and in the channels of the solid acid catalyst, and they will block the channels of the catalyst, thereby inactivating the catalyst. The catalyst needs to be regenerated once per 24 hours.

The department of chemical engineering of Tsinghua University has developed a novel alkylbenzene process using a modified β-zeolite solid acid catalyst. However, the modified β-zeolite catalyst is also prone to inactivation, having a short single pass lifetime, and thus needs to be regenerated repeatedly.

Existing methods of regenerating a solid acid catalyst comprise a hot benzene washing regeneration method and a carbon burning regeneration method. The conventional hot benzene washing regeneration method comprises stopping feeding of alkene into the reactor, instead of feeding benzene only, to wash the catalyst in the reactor. In the carbon burning regeneration method, a hot oxygen-lean gas at 650° C. is introduced into the reactor to remove the residues in channels by burning.

However, the conventional hot benzene washing regeneration method cannot remove all residues on the surface of and in the channels of the solid acid catalyst, because it is difficult for those materials to be removed by dissolving in hot benzene, resulting in gradual decrease in the single pass lifetime of the catalyst.

The carbon burning regeneration method has high requirements for the equipment and large energy consumption. Meanwhile, the channel structure of the catalyst will be permanently damaged after several rounds of high temperature carbon burning, resulting in permanent decrease in the catalytic activity and decrease in the long period lifetime of the catalyst.

SUMMARY

In view of this, the present inventors propose a method of regenerating a solid acid catalyst for benzene alkylation to improve the regeneration effect and prolong the lifetime of the catalyst.

In order to achieve the above object, the following technical solutions are used in the present disclosure.

A regeneration method for a benzene alkylation solid acid catalyst, comprising:
purging the solid acid catalyst in a reactor with a gas;
continuously injecting n-hexane at a feed port of the reactor and heating the n-hexane to wash the solid acid catalyst, and discharging the n-hexane entraining benzene alkylation reaction residues from a discharge port of the reactor; and
stopping injecting n-hexane, cleaning off a liquid in the reactor by purging with the gas, and cooling the reactor.

In some embodiments, the gas is nitrogen gas.

In some embodiments, a pressure of the gas is from 0.2 to 1.0 MPa.

In some embodiments, the pressure of the gas is from 0.3 to 0.8 MPa.

In some embodiments, the pressure of the gas is from 0.5 to 0.8 MPa.

In some embodiments, a duration of the purging is from 1 to 4 hours.

In some embodiments, the duration of the purging is from 2 to 3 hours.

In some embodiments, a heating temperature of the n-hexane is from 250° C. to 350° C.

In some embodiments, the heating temperature of the n-hexane is from 260° C. to 320° C.

In some embodiments, the heating temperature of the n-hexane is from 280° C. to 320° C.

In some embodiments, a duration of washing the solid acid catalyst with the n-hexane is from 9 to 12 hours, and preferably from 10 to 11 hours.

In some embodiments, the regeneration method further comprises taking a sample at the discharge port for observation, wherein when the sample turns from orange-yellow to clear and transparent, the regeneration is determined to be completed.

As compared to the conventional hot benzene washing regeneration method, the regeneration liquid used in the regeneration method of the present disclosure is n-hexane, which increases the solubility of the benzene alkylation reaction residues in the channels and enhances the regeneration effect. Meanwhile, the permanent damage to the channel structure of the catalyst caused by carbon burning regeneration is avoided, thereby prolonging the lifetime of the catalyst.

BRIEF DESCRIPTION OF DRAWINGS

FIG. 1 is a schematic diagram of a device used in an example of the present disclosure.

REFERENCE NUMBER LIST

1-Reactor; 2-Solid acid catalyst; 3-Feed pipe; 4-Gas supply pipe; 5-Discharge pipe; 6-In-line sampler.

DETAILED DESCRIPTION

In order to make the objects, technical solutions and advantages of the present disclosure more clear and apparent, the present disclosure will be further described in detail below in combination with particular embodiments and with reference to the drawings.

In the industrialized production of alkylbenzene, the inventors discover that when a solid acid catalyst is regenerated by washing with hot benzene, the isomerization and cracking products of alkane and alkene accumulated on the surface of and in the channels of the solid acid catalyst are not completely dissolved in the hot benzene, so that these materials cannot be completed removed, and thus the catalytic efficiency and lifetime of the solid acid catalyst will decrease continuously. After a number of experiments, it is discovered that n-hexane has a high dissolving capacity for the residues which are produced during the solid acid catalyzed alkylbenzene reaction and may block the channels of the catalyst, and thus has a higher removal capacity therefor than that of benzene. This is because benzene molecule has a cyclic structure and a large delocalized π-bond, so the molecule thereof occupies a large space, while n-hexane is a linear alkane, having small molecule volume, so that it can easily enter into the channels of zeolite to wash out the impurities.

On this basis, the inventors propose a modified method of regenerating a solid acid catalyst for benzene alkylation, comprising: purging the solid acid catalyst in a reactor with a gas; continuously injecting n-hexane at a feed port of the reactor and heating the n-hexane, and discharging the n-hexane entraining benzene alkylation reaction residues from a discharge port of the reactor; and stopping injecting n-hexane, cleaning off a liquid in the reactor by purging with the gas, and cooling the reactor.

In the method, the solid acid catalyst is a zeolite solid acid catalyst, the gas may be nitrogen gas, and a pressure of the gas may be from 0.2 to 1.0 MPa, for example, 0.3 MPa, 0.5 MPa, or 0.8 MPa. A duration of the purging with gas may be from 1 to 4 hours, for example, from 2 to 3 hours.

A duration of the washing with n-hexane may be from 9 to 12 hours, for example, 10 hours. A heating temperature may be from 250° C. to 350° C., for example, 260° C., 280° C. or 320° C. The washing with n-hexane and the heating may be carried out simultaneously.

In addition, the regeneration method may further comprise taking a sample at the discharge port for observation, wherein when the sample turns from orange-yellow to clear and transparent, the regeneration is determined to be completed.

The regeneration method may be carried out in a reactor for preparing alkylbenzene and the operation is simple. The regeneration method can save the regeneration time, and improve the production efficiency of alkylbenzene. Meanwhile, as compared to conventional regeneration methods, the catalytic activity of the regenerated catalyst may be recovered to 99% or more, the catalyst can be regenerated repeatedly, and the service life of the catalyst can be 8000 h or more.

Example 1

FIG. 1 is a schematic diagram of a device for preparing alkylbenzene in an example of the present disclosure. Here, the device comprises a reactor 1. A solid acid catalyst 2 is provided in the reactor 1. A feed pipe 3 and a gas supply pipe 4 are connected to the top of the reactor 1. The feed pipe 3 is configured to inject raw materials such as a mixture of an alkane and an alkene and benzene. A discharge pipe 5 is connected to the bottom of the reactor 1 for discharging alkylbenzene produced and unreacted raw materials. The discharge pipe 5 is provided with an in-line sampler 6.

A benzene alkylation reaction between the alkene and benzene occurs on the solid acid catalyst 2. When the efficiency of the benzene alkylation reaction decreases, it is required to regenerate the solid acid catalyst 2.

In regeneration, feeding is firstly stopped, and nitrogen gas at 0.5 MPa is introduced into the reactor 1 through the gas supply pipe 4, to purge the solid acid catalyst 2 in the reactor 1, with a purging duration of 2 hours.

Then, n-hexane is injected into the reactor 1 through the feed pipe 3 and is heated to 280° C., to wash the solid acid catalyst 2. The n-hexane entraining benzene alkylation reaction residues flows out of the reactor 1 through the discharge pipe 5, and the washing duration is 10 hours.

During this period, a sample may be taken through the in-line sampler 6 for observation, until the sample turns from orange-yellow to clear and transparent, at which time it can be determined that the regeneration is completed.

After the regeneration, the injection of n-hexane is stopped, nitrogen gas is introduced to clean off the liquid in the reactor 1 by purging, and the reactor is cooled to 150° C., thereby completing the regeneration process of the solid acid catalyst 2. At this time, the reactants may be introduced again to proceed with the production of alkylbenzene.

In existing technologies, after the solid acid catalyst is regenerated by using hot benzene, the initial conversion of materials is about 97%, while in the present disclosure, after the solid acid catalyst is regenerated by using n-hexane, the initial conversion of materials can be steadily 99% or more, and the lifetime of the solid acid catalyst is also prolonged accordingly, resulting in significant economic benefit in large scale production of alkylbenzene.

The above particular embodiments are used for describing the objects, technical solutions and advantageous effects of the present invention in detail. It should be understood that the above embodiments are only some particular embodiments of the present invention, but not intended to limit the present invention. Any variations, equivalents, modifications and the like made within the spirit and principle of the present invention should be included within the protection scope of the present invention.

The invention claimed is:

1. A regeneration method for a benzene alkylation solid acid catalyst, comprising:
   purging the solid acid catalyst in a reactor with a gas;
   continuously injecting n-hexane at a feed port of the reactor and heating the n-hexane to wash the solid acid catalyst, and discharging the n-hexane entraining benzene alkylation reaction residues from a discharge port of the reactor; and
   stopping injecting n-hexane, cleaning off a liquid in the reactor by purging with the gas, and cooling the reactor, wherein the gas is nitrogen gas, and
   wherein a pressure of the gas is from 0.2 to 1.0 MPa.

2. The regeneration method according to claim 1, wherein the pressure of the gas is from 0.3 to 0.8 MPa.

3. The regeneration method according to claim 2, wherein the pressure of the gas is from 0.5 to 0.8 MPa.

4. The regeneration method according to claim 1, wherein a duration of the purging is from 1 to 4 hours.

5. The regeneration method according to claim 4, wherein the duration of the purging is from 2 to 3 hours.

6. The regeneration method according to claim 1, wherein a heating temperature of the n-hexane is from 250° C. to 350° C.

7. The regeneration method according to claim 6, wherein the heating temperature of the n-hexane is from 260° C. to 320° C.

8. The regeneration method according to claim 7, wherein the heating temperature of the n-hexane is from 280° C. to 320° C.

9. The regeneration method according to claim 1, wherein a duration of washing the solid acid catalyst with the n-hexane is from 9 to 12 hours.

10. The regeneration method according to claim 1, wherein the regeneration method further comprises taking a sample at the discharge port for observation, wherein when the sample turns from orange-yellow to clear and transparent, the regeneration is determined to be completed.

11. The regeneration method according to claim 9, wherein a duration of washing the solid acid catalyst with the n-hexane is from 10 to 11 hours.

\* \* \* \* \*